(12) United States Patent
Cheindline et al.

(10) Patent No.: US 6,273,603 B1
(45) Date of Patent: Aug. 14, 2001

(54) MEASURING HEAD FOR USE IN RADIANT ENERGY FLASH MEASURING OF THE THERMAL DIFFUSIVITY OF SAMPLES

(75) Inventors: Mikhail Cheindline, Karlsruhe; Claudio Ronchi, Karlsdorf, both of (DE)

(73) Assignee: Euratom (LU)

( * ) Notice: Subject to any disclaimer, the term of this patent is extended or adjusted under 35 U.S.C. 154(b) by 0 days.

(21) Appl. No.: 09/319,776

(22) PCT Filed: Dec. 22, 1997

(86) PCT No.: PCT/EP97/07232

§ 371 Date: Jun. 11, 1999

§ 102(e) Date: Jun. 11, 1999

(87) PCT Pub. No.: WO98/28610

PCT Pub. Date: Jul. 2, 1998

(30) Foreign Application Priority Data

Dec. 23, 1996 (EP) .................................................. 96120836

(51) Int. Cl.[7] .............................. G01N 1/31; G01N 1/44; G01J 5/08

(52) U.S. Cl. ............................... 374/43; 374/44; 374/124

(58) Field of Search ................................ 374/43, 44, 102, 374/103, 104, 107, 121, 12, 124; 250/341.6, 341.2

(56) References Cited

U.S. PATENT DOCUMENTS

| | | | |
|---|---|---|---|
| Re. 28,954 | * 9/1976 | Baker et al. | 374/124 |
| 3,427,861 | * 2/1969 | Maley | 374/124 |
| 3,501,380 | * 3/1970 | Perch | 374/124 |
| 3,803,413 | * 4/1974 | Vanzetti et al. | 374/124 |
| 3,892,125 | * 7/1975 | Nunogaki | 374/43 |
| 4,243,327 | * 1/1981 | Frosch et al. | 374/43 |
| 4,557,607 | * 12/1985 | Busse | 374/124 |
| 4,591,272 | * 5/1986 | Morris et al. | 374/124 |
| 4,594,510 | * 6/1986 | Brown et al. | 374/43 |

(List continued on next page.)

FOREIGN PATENT DOCUMENTS

355065142A * 5/1980 (JP) ........................................ 374/43

OTHER PUBLICATIONS

Section E1, Week 9333, Oct. 6, 1993, Derwent Publications ltd., London, GB; Class S03, p. 5 AN 93–263630, Gorinskii, S.G. "Determination of Temperature Conductivity of Materials."

Section E1, Week 8441 Nov. 21, 1984, Derwent Publications Ltd., London, GB; Class S03, p. 4, AN 84–255514, Beezin, V. V. et al., "Materials thermo–physical properties determination."

(List continued on next page.)

*Primary Examiner*—Diego Gutierrez
*Assistant Examiner*—Madeline Gonzalez
(74) *Attorney, Agent, or Firm*—Finnegan, Henderson, Farabow, Garrett & Dunner, L.L.P.

(57) ABSTRACT

The invention refers to a measuring head for use in radiant energy flash measuring of the thermal diffusivity of heterogeneous samples (S) under employment of a probe beam (B) generated by a radiant energy generating means and a detector means for detecting a temperature rise of the sample (S), comprising a sample holder means (SH) for receiving the sample (S). The technical problem to be solved is to provide a measuring head offering the opportunity to align the sample (S) with the probe beam (B) in order to carry out local measurements of the thermal diffusivity in the axial direction of the sample (S) or to deposit the energy shot on the most suitable area of the sample (S), dependently on the given sample features. Therefore, according to the present invention it is proposed to arrange the sample holder means (SH) movable in at least one direction (X, Y) perpendicular to the optical axis (AB) of the probe beam (B).

10 Claims, 4 Drawing Sheets

U.S. PATENT DOCUMENTS

| | | | |
|---|---|---|---|
| 4,853,541 | * | 8/1989 | Duhrkoop ............................. 374/124 |
| 4,874,251 | * | 10/1989 | Thomas et al. ...................... 374/124 |
| 5,085,073 | * | 2/1992 | Heyman et al. ..................... 374/124 |
| 5,478,151 | * | 12/1995 | Duhrkoop ............................. 374/124 |
| 5,667,300 | * | 9/1997 | Mandelis et al. ...................... 374/43 |
| 5,688,049 | * | 11/1997 | Govorkov .............................. 374/43 |
| 5,760,400 | * | 6/1998 | Prekel et al. ...................... 250/341.6 |
| 5,923,036 | * | 7/1999 | Tague, Jr. et al. ................ 250/341.2 |
| 6,062,729 | * | 5/2000 | Ni et al. ............................... 374/124 |
| 6,074,087 | * | 6/2000 | Chen et al. .......................... 374/124 |

OTHER PUBLICATIONS

Patent Abstracts of Japan, Pub. No. 62197754, Sep. 1, 1987.

Section E1, Week 9333, Oct. 6, 1993, Derwent Publications Ltd., London, GB; Class S03, p. 4, AN 93–263629, Gorinskii, S. G., "Materials conductivity temperature determination."

Review of Scientific Instruments, vol. 63, No. 4, Apr. 1, 1993, Kosky, P.G. "A method of Measurement of thermal conductivity: Application to free–standing diamond sheet."

Review De Physique Appliquae, vol. 20, No. 1, Jan. 1985, Pawloski et al., "Analysis of boundary conditions and transient signal treatment in diffusivity measurents of laser pulse method."

Patent Abstracts of Japan, Pub. No. 55065142, May. 16, 1980.

W.J. Parker et al.: "Flash Method of Determining Thermal Diffusivity; Heat Capacity and Thermal Conductivity," J. Appl. Phys. 32 (9), 1679–1684 (1961).

R. E. Taylor et al.: Compendium of Thermophysical Property Measurement Methods 2 (K.D. Maglic, A Cezairilyan & Ve. E. Peletsky, eds.) 281–314, Plenum Press, New York (1991.

K.D. Maqlic et al.: High Temperatures—High Pressures, 1980, vol. 12, pp. 555–560.

* cited by examiner

MEASURING HEAD FOR USE IN RADIANT ENERGY FLASH MEASURING OF THE THERMAL DIFFUSIVITY OF SAMPLES

BACKGROUND OF THE INVENTION

1. Field of the Invention

The present invention refers to a measuring head for use in radiant energy flash measuring of the thermal diffusivity of heterogeneous samples, in particular of heterogeneous highly radioactive samples or other samples for which remote manipulation is required.

2. Description of the Related Art

From W. J. Parker, R. J. Jenkins, C. P. Butler and G. L. Abbot, J. Appl. Phys. 32(9), 1679–1684 (1961) the so-called "flash method" for measuring the thermal diffusivity "a" is known. In this method the front face of a small disc-shaped specimen or sample is subjected to a very short burst of radiant energy coming from a laser or a flash lamp. The method employs irradiation times in the order of one millisecond. The resulting temperature rise of the rear surface of the sample is measured and recorded, and then thermal diffusivity values are computed from temperature rise versus time.

The simplest and most frequently used way to calculate thermal diffusivity is to use $t_{1/2}$ as a characteristic time, i.e. the time needed for the rear side temperature to reach 50% of its maximum value:

$$a = 0.1388 L^2 / t_{1/2} \ (m^2/s)$$

From R. E. Taylor and K. D. Maglic, in: Compendium of Thermophysical Property Measurement Methods 2 (K. D. Maglic, A. Cezairliyan and V. E. Peletsky, eds.) 281–314, Plenum Press, New York (1991) a method for carrying out a transient temperatur measurement is known. The detector for measuring the transient temperature may be a thermocouple, a infrared detector or an optical pyrometer. The detector must be capable to record 0.1 degree change above the ambient temperature. The response time of the detector/amplifier combination must be less than 10% of $t_{1/2}$.

FIG. 4 illustrates schematically the known method for measuring the thermal diffusivity.

The prior art measuring heads for carrying out the above described method for measuring the thermal diffusivity are used in connection with lasers as a radiant energy generating means and a detector means for detecting a temperature rise at the rear side of the sample. They comprise a sample holder means for receiving the sample to be measured. However, they are all constructed in view of producing and analysing a pre-fixed type of temperature spike. They in particular do not offer the opportunity to align the sample with the probe beam generated by the laser. Thus the energy shot cannot be deposited on the most suitable area, dependently on the given sample features, and a local axial diffusion measurement cannot be performed.

SUMMARY OF THE INVENTION

Therefore, it is the object of the present invention to provide a measuring head for use in radiant energy flash measuring of the thermal diffusivity of heterogeneous samples by means of which local measurements of the thermal diffusivity can be carried out without substituting the sample holder.

According to the present invention it is proposed to provide a measuring head for use in radiant energy flash measuring of the thermal diffusivity of heterogeneous samples under employment of a probe beam generated by a radiant energy generating means and a detector means for detecting a temperature rise of the sample, comprising a sample holder means for receiving the sample with a sample holder means which is movable in at least one direction perpendicular to the optical axis of the probe beam. Preferably, a laser is used as a radiant energy generating means but a flash lamp or other suitable means for generating a probe beam can be employed.

The measuring head according to the present invention offers the advantage that the sample can be easily aligned with the probe beam generated by the radiant energy generating means in order to carry out local measurements of the thermal diffusivity and to deposit the energy shot on the most suitable area of the sample, dependently on the given sample features.

According to further features of the present invention the measuring head has an adjustable viewing head for shifting a detector probe spot from a first position on the sample to a second position on the sample.

Thus, it is made possible to change the measurement method from axial diffusion measurement to radial diffusion measurement without substituting the sample holder. The viewing head optics comprising substantially a mirror having a field stop hole determining the field of the sample to be measured can be adjusted and thereby focused on an arbitrary zone of the sample surface independently of the position and size of the probe beam spot. Therefore, in non-homogeneous samples the diffusivity can be measured in different positions by using the radial analytical method without moving the sample and disturbing the background temperature provided by a furnace means surrounding the sample. Finally, thanks to the mirror of the viewing head optics, on which the field stop aperture is located, a full image of the sample is obtained, enabling the coordinates of the measured area to be accurately determined.

Thus, the present invention provides a multipurpose measuring head for measuring the thermal diffusivity.

Since in particular highly radioactive samples are to be measured it is important to keep all delicate parts involved like the radiant energy generating means, the detector and the preamplifiers at an arbitrary distance from the sample. This is achieved by employing optical fibers for transmitting the light emitted by the sample and seen by the field stop hole to the detector and for transmitting the radiant energy from the radiant energy generating means to a radiant energy input means delivering the probe beam into a lead-shielded cell containing the furnace means, an objective, the mirror and the sample holder means.

The radiant energy input means being movable in at least one direction perpendicular to the optical axis of the probe beam offers the advantage that the probe beam spot can be focused on areas of arbitrary sizes, making it possible to create the optimal temperature-spike conditions for the envisaged measurement method. Said radiant energy input means is arranged on one side of the sample holder while said adjustable viewing head is arranged on the opposite side of the sample holder. In other words, said probe beam is directed to one side of the sample while said adjustable viewing head is directing a detector probe spot on an arbitrary zone on the opposite side of the sample.

The adjustable viewing head additionally has a telescope for monitoring the shifting movement of the detector probe spot and the objective is arranged for focussing the light emitted by the sample to the viewing head.

The sample holder means is detachably fixed to the furnace means surrounding the sample. Thus, the furnace means is movable together with the sample holder means. Preferably, the furnace means consists of at least one high frequency (HF) coil and thermic shields which facilitates a movement of the furnace means and the sample holder means even when the measuring head according to the present invention is in operation.

BRIEF DESCRIPTION OF THE DRAWINGS

One embodiment of the present invention is now described under reference to the attached drawings.

DESCRIPTION OF THE PREFERRED EMBODIMENT

Figure 1:
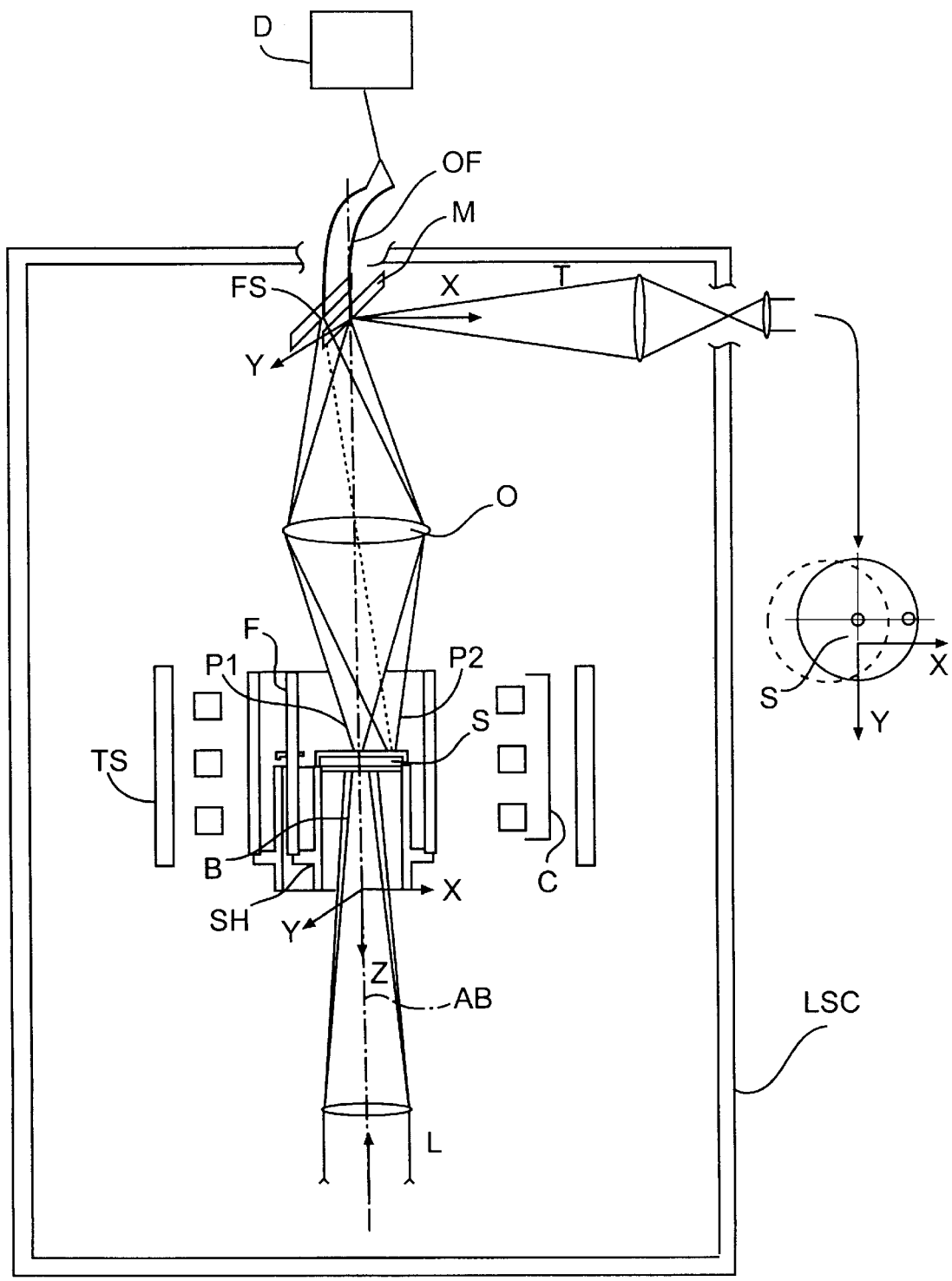
FIG. 1 shows schematically the design of an embodiment of the measuring head according to the present invention.

The embodiment shown in FIG. 1 is used in connection with a laser (not shown) as radiant energy generating means. Therefore, the term "laser" is used in the following detailed description instead of the term "radiant energy".

Further, the Z-direction in FIG. 1 is identified as the "axial direction" whereas the X- and Y-directions in FIG. 1 are related to the term "radial direction" where appropriate.

The measuring head for use in laser flash measuring of the thermal diffusivity illustrated in FIG. 1 comprises a laser input means consisting of at least one lense L, a sample holder SH being movable in X-Y-directions, a furnace comprising a high frequency (HF) coil C having thermic shields, TS shown schematically in FIG. 1 an objective O and an adjustable viewing head. The viewing head has a mirror M with a field stop hole FS and optical fibers OF for transmitting light emitted by the rear or upper side of the sample S supported by the sample holder SH to the detector D, depicted schematically in FIG. 1. These components of the measuring head are independent mechanical moduls which can be readily removed by means of manipulators and, in cases of major failures, replaced. Further, the furnace F, the sample holder SH and the optical parts like the lense L, the objective O and the mirror M are designed for implementation in a lead-shielded cell such as cell LSC also depicted schematically in FIG. 1 where no access will be eventually available for repairs and maintenance except that allowed by two remote-hand manipulators.

In FIG. 1 said laser input means, i. e. said lense L, is arranged below the sample holder SH while said adjustable viewing head and said objective O are arranged above sample holder SH. In other words, the spot of the probe beam B generated by said laser is directed to the front or lower side of sample S by said lense L while said objective O is focusing the light emitted by the rear or upper side of sample S to the viewing head.

The stationary-temperature detector receiving the light transmitted by the optical fibers OF may be a an infrared detector or an optical pyrometer. Further, for transient temperature measurements a InGaAs and Si photodiode detector provided with a special low noise preamplifier with wide variable offset can be used which allows compensation for background Plank radiation in the range of 800–2500 K. The suitable detectors which are particularly sensitive to nuclear radiation damage are placed outside the cell, the light being transmitted through the optical fibers OF which can be easily plugged in and out and can thus be replaced when they become nearly darkened by the γ-radiation. The lenses of the objective O placed within the HF furnace housing are protected by a pivoting tungsten shield, which is removed only during the short measurement time, against direct nuclear radiation of the sample S.

The main advantage of the use of HF heating instead of direct electrical heating of the furnace F is the availability of replacing of the furnace F without any electrical connections and enables one to move the furnace F together with the sample holder SH even when in operation (as shown schematically in FIG. 1). Thus, the design of this furnace means will allow a sample S within the sample holder SH and furnace F to be precisely and remotely moved in X-Y-directions. One of the reasons of this precise positioning of the sample S is to allow one to choose the exact local point of the sample S to be measured. Thus, the thermal diffusivity in the axial direction of the disc-shaped sample S can be measured at a plurality of local points of the sample S which is of particular importance when dealing with the non-homogeneous materials. This measurement method is called local axial diffusion measurement.

The sample holder SH allows the operator of the measuring head according to the present invention to change the sample S remotely with the help of manipulators.

The alignment of the system laser probe beam B/sample S/field stop hole FS is ensured by a coarse X-Y-adjustment of the laser input means comprising at least one lense L for focusing the laser probe beam B to the sample S, followed by a micrometric X-Y-Z-displacement of the mirror M at the center of which lies the field stop hole FS corresponding to the measured field of the sample S. The center of this hole or aperture is, under the optimum measurement conditions, aligned with the laser probe beam B. Based on this initial alignment, the position of the sample S mounted in a graphite sample holder SH can be varied as the latter is fixed to a micrometric X-Y-table moved by precision stepper motors. Thus, a desired spatial resolution of the axial diffusion measurement can be precisely controlled.

The whole surface of the sample S can be observed through the mirror M, whilst only the area projected onto the field stop hole FS is seen and thus detected by the detector. The measuring head according to the present invention enables the operator with the help of a telescope T arranged at the adjustable viewing head to find proper measurement conditions even in cases where the sample platelet has an irregular shape or when the holder cannot be reproducibly positioned in the furnace F.

A further advantage of a precise positioning of the mirror M with the field stop hole FS is to ensure the well reproducible shifting of the detector probe spot from a position P1 represented by the optical axis AB of the laser probe beam B to a position P2 being radially spaced apart from position P1. Such a radial movement of the detector probe spot enables the operator to perform the measurement of the thermal diffusivity of the sample S in a radial direction. This measurement method is called radial diffusion measurement and has been described by R. E. Taylor and K. D. Maglic, in: Compendium of Thermophysical Property Measurement Methods 2 (K. D. Maglic, A. Cezairliyan and V. E. Peletsky, eds.) 281–314, Plenum Press, New York (1991).

Thus, the measuring head according to the present invention can also perform a multipurpose operation directed to a measurement of the thermal diffusivity according to both the local axial diffusion measurement method and the radial diffusion measurement method.

In order to keep not only the detector and preamplifiers at an arbitrary distance from the radioactive sample S but also the laser delivering the probe beam B additional optical fibers (not shown) are provided for transmitting the laser radiation from the remotely arranged laser to the lense L which is also disposed within the lead-shielded cell.

The parts in the vicinity of the sample S and hence exposed to γ-radiation are the rather insensitive mirror M, the lense L and the easily replaceable objective consisting of at least one lense O.

Figure 2:
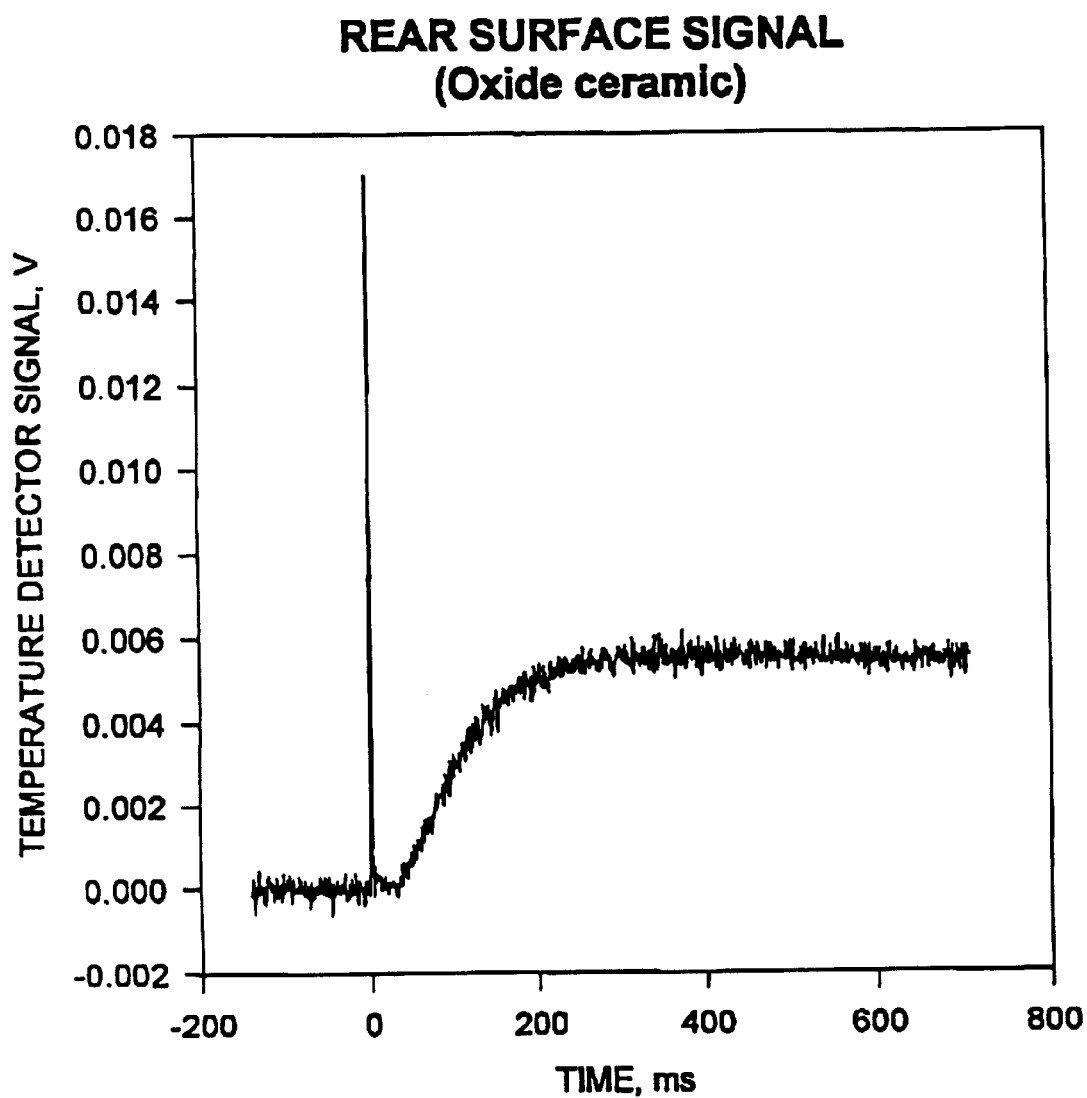
FIG. 2 shows a temperature detector signal versus time measured by means of a measuring head according to the present invention.

The measuring head according to the present invention has been tested with graphite and ceramic zirconia samples S. FIG. 2 shows the signal detected on the face opposite to that hit by the laser probe beam B. The laser light diffusely reflected during the millisecond (ms) pulse produced a significant disturbance. However, this perturbation has been eliminated by inserting a special multilayer optical filter. The transient recorder used provides 12 bits of resolution to reduce quantisation noise. Signal-to-noise ratios in the order of 1/100 and even more in some cases have been achieved with deposited pulse energies of the order of 10 $J/cm^2$.

Figure 3:
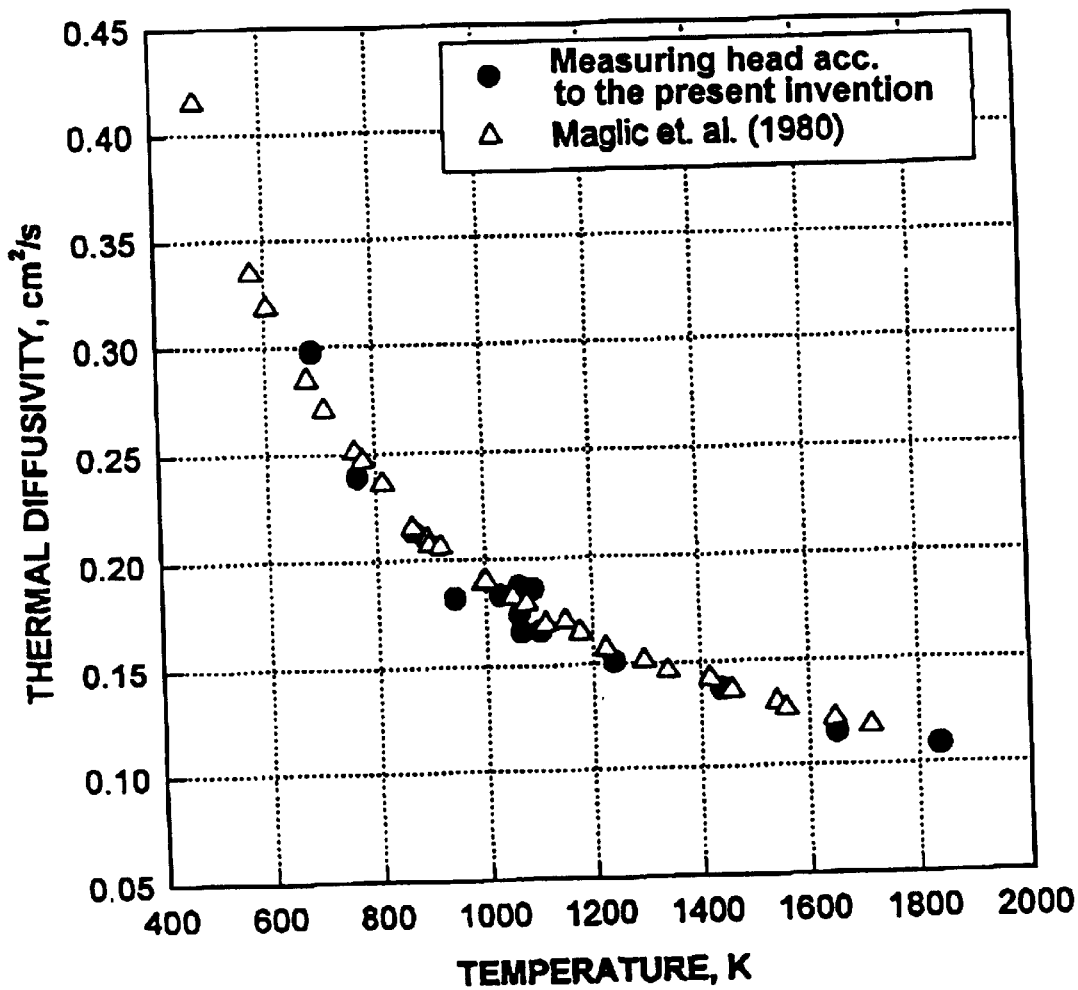
FIG. 3 shows the thermal diffusivity versus temperature measured by means of a measuring head according to the present invention in comparison with the data according to K. D. Maglic, N. L. Perovic and Z. P. Zivotic, High Temp. High Pressures. 12, 555–560 (1980).
Figure 4:
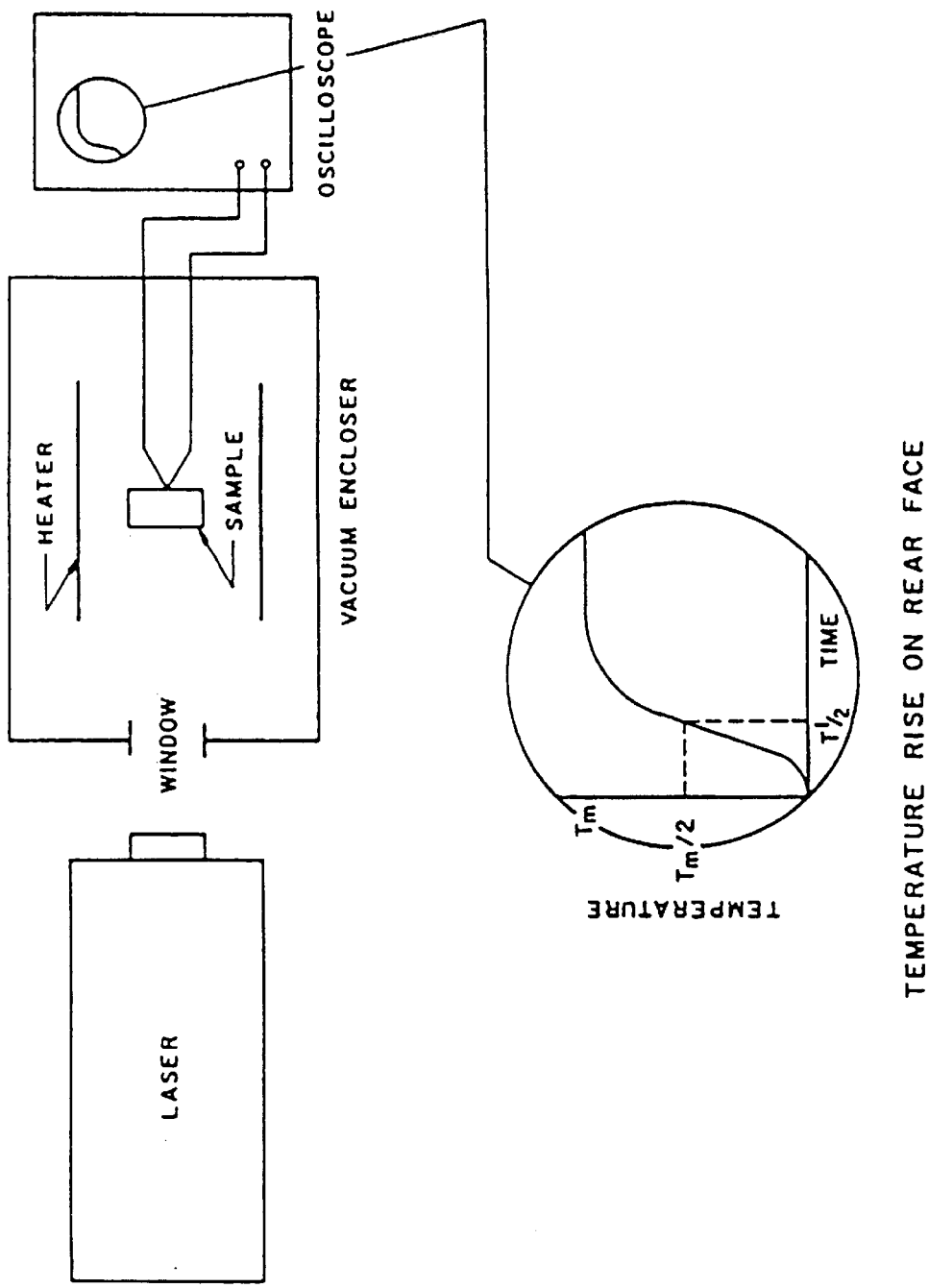
FIG. 4 shows schematically a known prior art method for measuring the thermal diffusivity described by W. J. Parker, R. J. Jenkins, C. P. Butler and G. L. Abbot, J. Appl. Phys. 32(9), 1679–1684 (1961).

FIG. 3 shows experimental data on POCO grade graphite derived by means of the measuring head according to the present invention in comparison with data measured by K. D. Maglic, N. L. Perovic and Z. P. Zivotic, High Temp. High Pressures. 12, 555–560 (1980).

In order to enable a working in the lead-shielded cell under strong γ-irradiation conditions the measuring head according to the present invention can be designed to permit one to replace the sample S, the sample holder SH, the HF-coil C and all optical elements like the mirror M and the lenses O and L remotely with the aid of manipulators.

The measuring head, the laser and the detector means used for the above mentioned measurements had the following characteristics:
1. Temperature range: 500–2.000° C.
2. Furnace F: Graphite with HF heating at 330 kHz frequency
3. Sample size: Diameter×thickness=4–10 mm×1–2 mm
4. Sample holder SH: Graphite, with precise remote X-Y ±5 mm positioning
5. Probe laser:
   Energy: 0–10 J
   Pulse length: 100 $\mu$s–10 ms continuously variable
   Wavelength: 1.06 $\mu$m
   Laser beam delivery system: Fiber optic with 1 mm core
   Beam size: Diameter=3 mm (can be reduced to 1.5 mm for the "radial diffusion measurement method"-operation)
6. Atmosphere: Vacuum or reduced pressure gas at low temperatures
7. Back temperature measurement system:
   Sensor: InGaAs or Si photodiode
   Temperature sensitivity of the detector: 0.01 K
   Optical system: Achromatic objective with fiber optic and precision viewing system
   Automatic gray filter changing for covering of broad temperature range
   Spot size of temperature measurement: 1.0 or 0.1 mm in diameter
   Recording system: Transient recorder with 12 bit resolution and 256 K words memory
   Amplifier: Bandwidths DC-3 kHz with background signal subtraction
   Precise positioning of the probe spot: X-Y-Z ±10 mm
8. Measuring method:
   a) axial, with 1 mm spatial resolution
   b) radial

What is claimed is:

1. Measuring head for use in radiant energy flash measuring of the thermal diffusivity of heterogeneous samples under employment of a probe beam generated by a radiant energy generating means and a detector means for detecting a temperature rise of said sample, comprising
   a sample holder means for receiving said sample, wherein said sample holder means is movable in at least one direction perpendicular to the optical axis of said probe beam,
   a radiant energy input means for focusing said probe beam to said sample, and
   an adjustable viewing head for shifting a detector probe spot from a first position on said sample to a second position on said sample,
   wherein said radiant energy input means is arranged on one side of said sample holder means while said adjustable viewing head is arranged on the opposite side of said sample holder means.

2. Measuring head according to claim 1, wherein said viewing head comprises a mirror being movable in directions perpendicular and/or parallel to said axis and having a field stop hole determining the field of said sample to be measured.

3. Measuring head according to claim 2, wherein said viewing head has first optical fibers for transmitting the light emitted by said sample and seen by said field stop hole to said detector means.

4. Measuring head according to one of claims 1, 2, or 3, wherein said viewing head has a telescope for monitoring said shifting movement of the detector probe spot.

5. Measuring head according to one of claims 1 through 3, wherein it comprises an objective for focusing radiation emitted by said sample to said viewing head.

6. Measuring head according to one of claims 1–3 wherein said sample holder means is detachably fixed to a furnace means surrounding said sample, said furnace means being movable together with said sample holder means.

7. Measuring head according to claim 6, wherein said furnace means comprises at least one high frequency coil and thermic shields.

8. Measuring head according to one of claims 1–3, wherein said radiant energy input means is movable in at least one direction perpendicular to said optical axis.

9. Measuring head according to one of claims 1–3 wherein second optical fibers are provided for transmitting the radiant energy from said radiant energy generating means to said radiant energy input means.

10. Measuring head according to claim 2 wherein said radiant energy input means, said mirror, and said sample holder means are implemented in a lead-shielded cell.

* * * * *

UNITED STATES PATENT AND TRADEMARK OFFICE
CERTIFICATE OF CORRECTION

PATENT NO. : 6,273,603 B1
DATED : August 14, 2001
INVENTOR(S) : Mikhail Cheindline et al.

It is certified that error appears in the above-identified patent and that said Letters Patent is hereby corrected as shown below:

<u>Column 6, claim 2,</u>
Line 35, before "axis", insert -- optical --.

Signed and Sealed this

Second Day of April, 2002

Attest:

JAMES E. ROGAN
*Director of the United States Patent and Trademark Office*

*Attesting Officer*